United States Patent [19]

Rideout et al.

[11] Patent Number: 5,177,083
[45] Date of Patent: Jan. 5, 1993

[54] DRUGS EFFECTIVE AGAINST RETROVIRUSES

[75] Inventors: Darryl C. Rideout, Del Mar; John Elder, Encinitas, both of Calif.

[73] Assignee: The Scripps Clinic and Research Foundation, La Jolla, Calif.

[21] Appl. No.: 405,834

[22] Filed: Sep. 11, 1989

Related U.S. Application Data

[63] Continuation-in-part of Ser. No. 261,436, Oct. 24, 1988, which is a continuation-in-part of Ser. No. 108,833, Oct. 14, 1987, Pat. No. 4,812,449, which is a continuation-in-part of Ser. No. 906,143, Sep. 11, 1986, abandoned, which is a continuation-in-part of Ser. No. 882,082, Jul. 3, 1986, abandoned.

[51] Int. Cl.⁵ ............... A61K 31/505; A61K 31/155; A61K 31/15
[52] U.S. Cl. .................................. 514/296; 514/632; 514/639; 514/664; 514/666
[58] Field of Search ............... 514/183, 296, 632, 639, 514/664, 666

[56] References Cited

U.S. PATENT DOCUMENTS

| | | | |
|---|---|---|---|
| 4,200,436 | 4/1980 | Mochida et al. | 23/30 B |
| 4,215,102 | 7/1980 | Lee | 424/3 |
| 4,460,560 | 7/1984 | Tokes et al. | 424/1.1 |

FOREIGN PATENT DOCUMENTS 0277330 7/1987 European Pat. Off.
2547184 11/1984 France .

8800047 1/1988 PCT Int'l Appl. .

OTHER PUBLICATIONS

Desfosses et al., *Analytical Biochem.* (1986) 159:179–186.
Balzarini, et al., *Int. J. Cancer* (1986) 37:451–457.
Levine, et al., *Annals Int. Med.* (1986) 105:32–37.
Broder, et al., *Lancet* (1985) 1:627–630.
De Clercq, *Cancer Letters* (1979) 8:9–22.
Ho, et al., *New Eng. J. Med.* (1987) 317:278–286.
Klatzmann, et al., *Immunol. Today* (1986) 7:291–296.
Siliciano, et al., *Cell* (1988) 54:561–575.
Pauza, *Cellular Immunol.* (1988) 112:414–424.
Pauza, et al., *J. Virol.* (1988) 62(10):7.
Jentsch, et al., *J. G. Virol.* (1987) 68:2183–2192.
Pedersen, et al., *Science* (1987) 235:790–793.
Steinman, et al., *J. Cell Biol.* (1976) 68:665–687.
Besterman, et al., *J. Cell Biol.* (1981) 91:716–727.
Richman, et al., *J. Exp. Med.* (1987) 166:1144–1149.
Cheson, et al., *JAMA* (1987) 258(10):1347–1351.
Spingarn, et al., *J. Med. Chem.* (1979) 22(11):1314–1316.
Murdock, et al., *J. Med. Chem.* (1982) 25(5):505–518.

*Primary Examiner*—John W. Rollins
*Attorney, Agent, or Firm*—Morrison & Foerster

[57] ABSTRACT

A method to treat or prevent retroviral infection by administering a novel conjugate is described. Lucifer Yellow and its analogs are conjugated to compounds having carbonyl functional groups for reaction with the semicarbazide moiety of Lucifer Yellow to obtain the semicarbazone conjugate.

7 Claims, 12 Drawing Sheets suramin

DRUGS EFFECTIVE AGAINST RETROVIRUSES

CROSS-REFERENCE TO RELATED APPLICATION

This is a continuation-in-part of U.S. Ser. No. 261,436 filed Oct. 24, 1988 which is a continuation-in-part of U.S. Ser. No. 108,833, filed Oct. 14, 1987, now U.S. Pat. No. 4,812,449 which is a continuation-in-part of U.S. Ser. No. 06/906,143, filed Sep. 11, 1986, now abandoned, which is a continuation-in-part of U.S. Ser. No. 882,082, filed Jul. 3, 1986, now abandoned.

TECHNICAL FIELD

The invention relates to materials which are useful in treating or inhibiting retroviral infection. More specifically, it concerns semicarbazones of Lucifer Yellow and its analogs which are effective in inhibiting human immunodeficiency virus (HIV) and other retroviral infections.

BACKGROUND ART

There are a number of viral diseases recognized as retroviral in origin in both humans and other animals. The most publicized such disease among humans is that caused by the human immunodeficiency virus (HIV) as either AIDS or ARC. Other such diseases, however, include hepatitis B and hepatitis delta. Among cats, retroviral diseases include those caused by the feline immunodeficiency virus (FIV) and the feline leukemia virus (FeLV). A number of other animal species also contract retroviral-caused infections, such as the Visna virus infections of ungulates.

There have been a number of approaches to the treatment of such diseases, none of them entirely successful. Over a million Americans and several million people worldwide are infected with HIV, and treatment with the experimental drug AZT, produced by Burroughs Wellcome, appears to be of some help although it is clear that AZT is unable to cure AIDS and is extremely toxic. Nevertheless, AZT has been a considerable commercial success. There is no doubt that there is a continuing need for more effective antiviral agents which are effective against retroviral infections in general, and against HIV in particular.

A related approach to that herein is described in PCT Application WO88/00047, published Jan. 14, 1988 and incorporated herein by reference. This application describes various materials which can be administered separately to a microenvironment and there assembled to create an active conjugate. The copending parent application herein, U.S. Ser. No. 261,436, also incorporated herein by reference, focuses on microenvironment of retroviral infections, specifically the loci of infection by human immunodeficiency virus (HIV), and the possibility to administer nontoxic precursors of a drug which would self-assemble at the site of the HIV infection as advantageous in treating the disease and symptomology caused by this virus.

The present application, rather than relying on self-assembly at the site of infection, is directed to administering compounds which are preassembled, and which are related to those used as components in the assembly in the parent application. Certain additional art discusses compounds which are also related to those described and claimed herein.

The compound most closely related to the invention conjugates described herein is suramin sodium, which is a complex conjugate of trisodium sulfonate naphthyl derivatives and aromatic nuclei linked through amide linkages. The structure of suramin is The effects of suramin on the treatment of AIDS and its mechanism of action have been studied by a number of workers (Balzarini, J., et al, *Int J Cancer* (1986) 37:451-457; Levine, A. M., et al, *Annals Int Med* (1986) 105:32-37; Broder, S., et al, *Lancet* (1985) 1:627-630; Cheson, B. D., et al, *JAMA* (1987) 258:1347-1351). In general, this compound has been found helpful in treatment, although its toxicity precludes its use as a single agent in treatment. Side effects include ophthalmic damage, hypoadrenalism, nausea, thrombocytopenia and vomiting, and some deaths have been attributed to these side effects.

Figure 1:
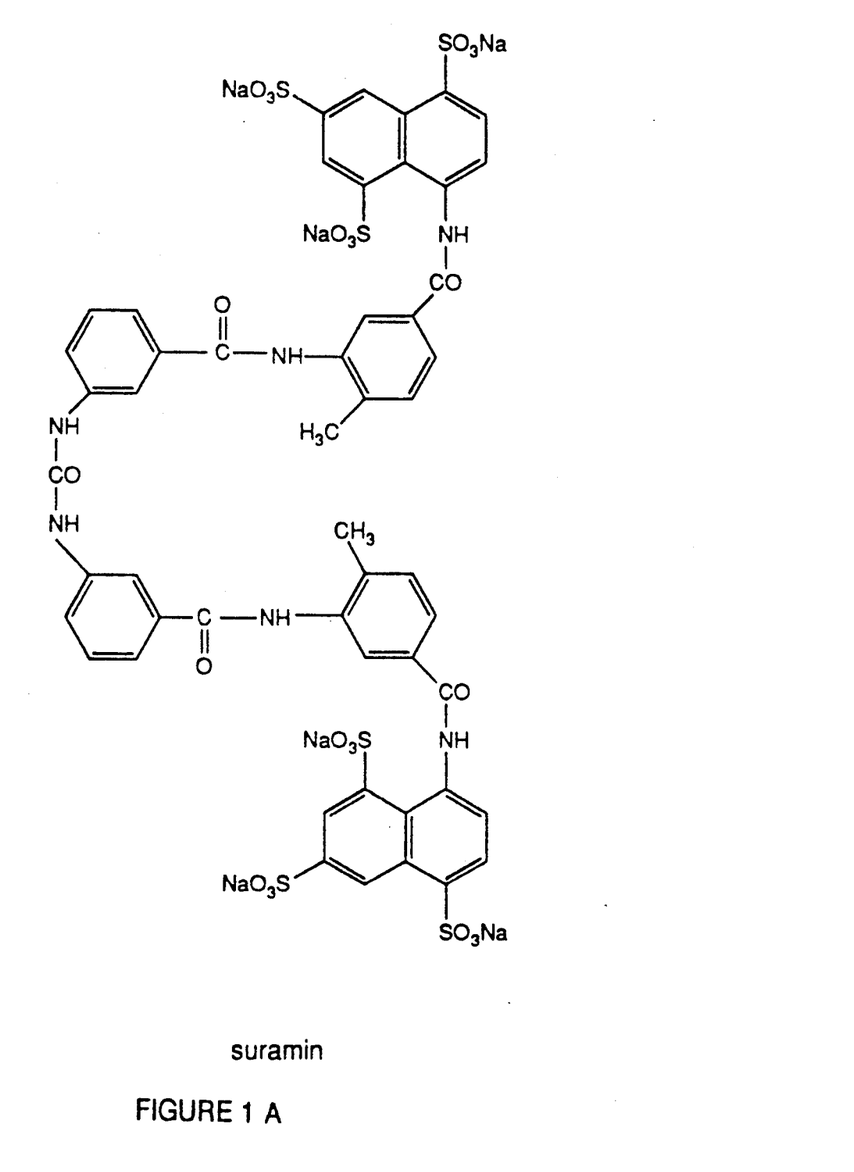
FIG. 1A shows suramin sodium.
FIG. 1B shows an analog of suramin sodium.
FIG. 1C shows an analog of suramin sodium.
FIG. 1D shows an analog of suramin sodium.
FIG. 1E shows an analog of suramin sodium.
FIG. 1F shows an analog of suramin sodium.
FIG. 1G shows an analog of suramin sodium.
FIG. 1H shows an analog of suramin sodium.
FIG. 1I shows an analog of suramin sodium.
FIG. 1J shows an analog of suramin sodium.
Figure 1B:
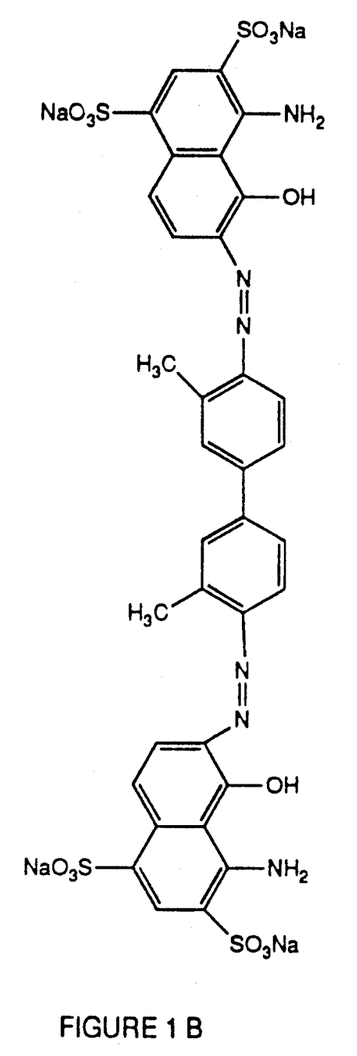
Figure 1C:
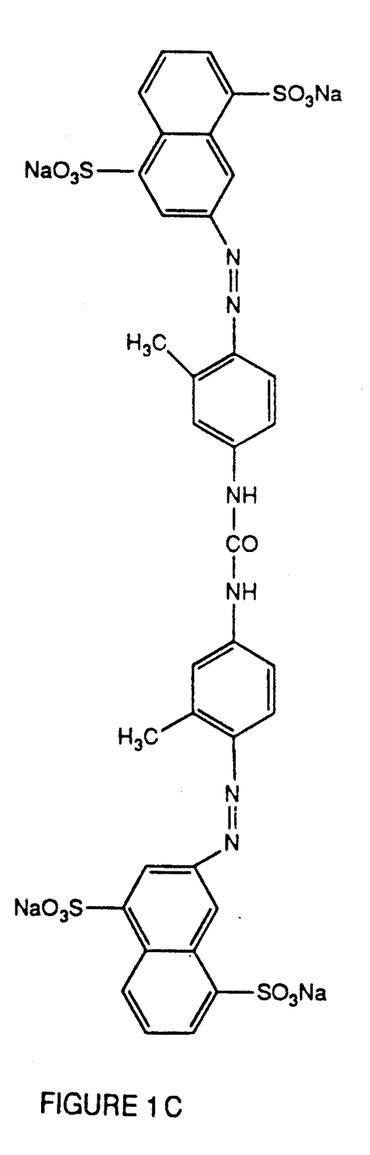
Figures 1D, 1E:
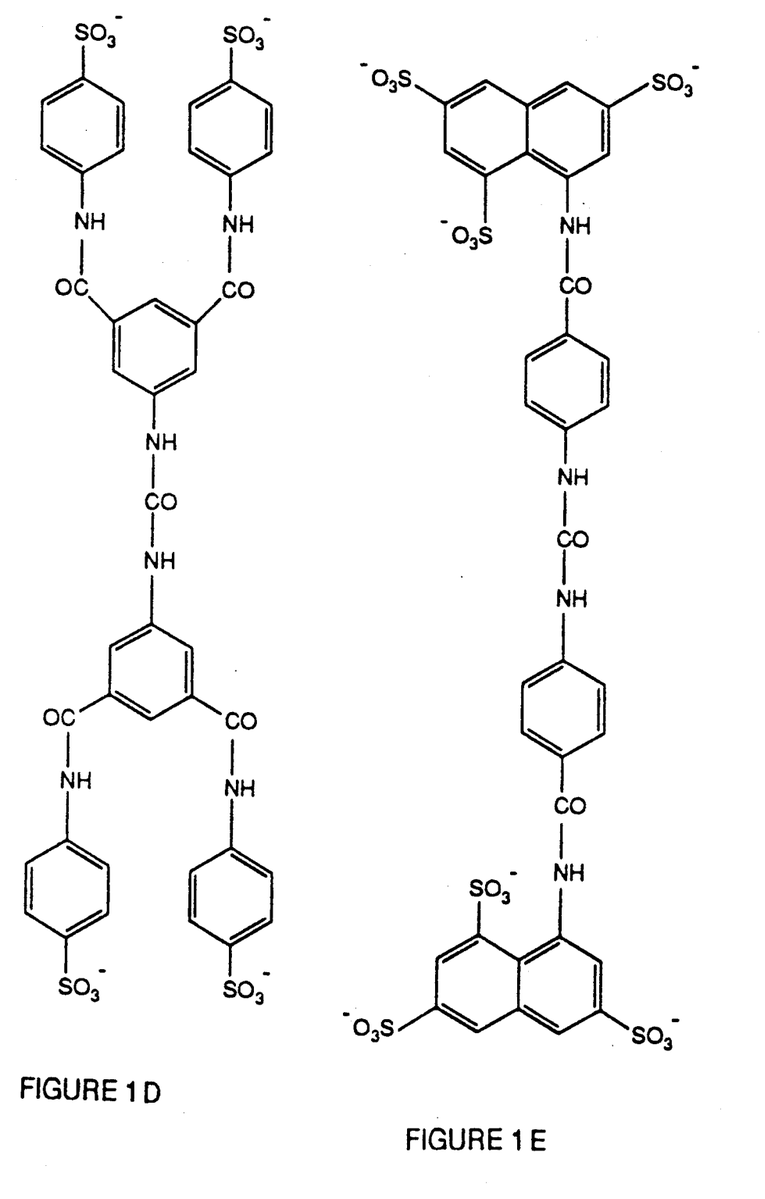
Figure 1F:
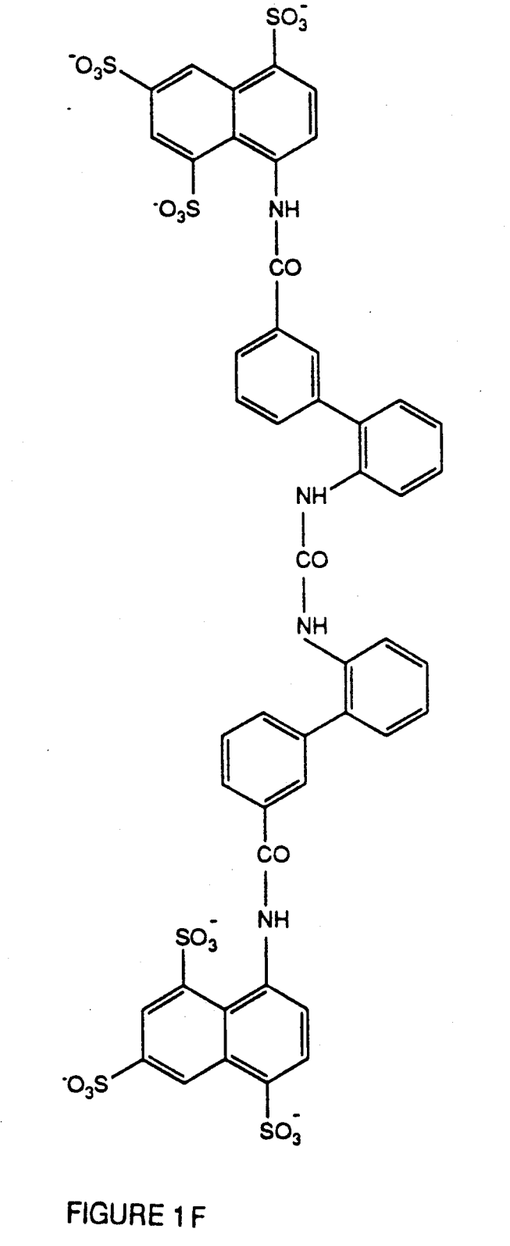
Figure 1G:
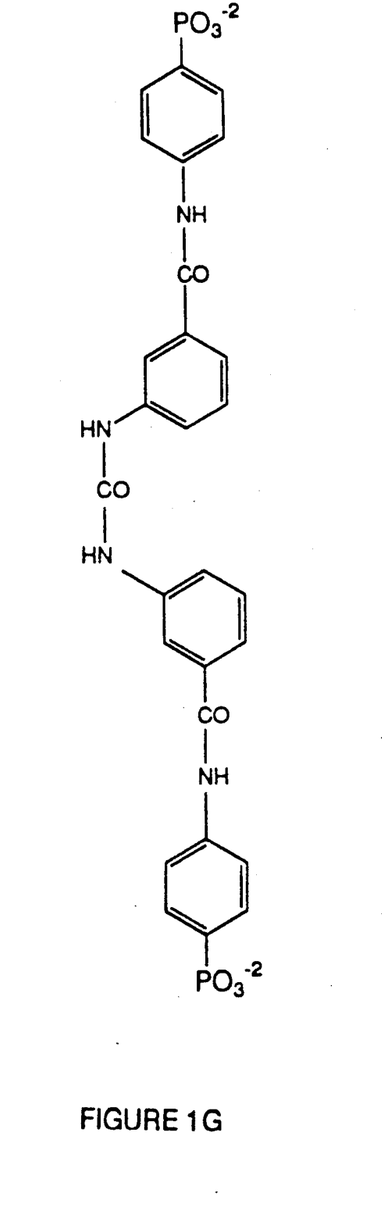
Figure 1H:
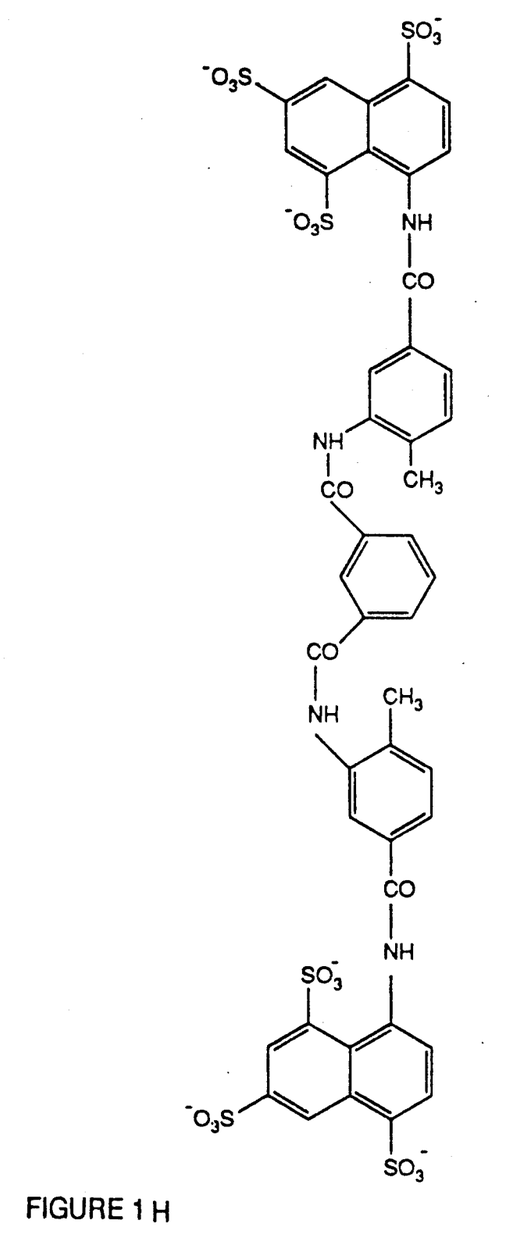

It has been suggested that the antiviral mechanism of suramin is due to binding of the polyanionic molecule to reverse transcriptase (DeClercq, E., *Cancer Lett* (1979) 8:9-22) and a large number of suramin analogs have been prepared. A total of 90 suramin analogs, of which 57 showed the ability to inhibit HIV-I reverse transcriptase activity, and 24 of which were superior to suramin in this inhibition, were prepared by Jentsch, K. D., et al, *J Gen Virol* (1987) 68:2183-2192. A representative group of suramin analogs is shown in FIG. 1. All of these are bis(naphthalene polysulfonic) acids, show $ID_{50}$ values in the range of 5-42 ug/ml and, like suramin, eliminate the cytopathic effect of HIV-I against MT4 cells at 50 ug/ml.

As stated above, suramin sodium is highly toxic; too toxic to be used clinically to treat HIV infection. The analogs so far prepared have similar drawbacks.

The conjugates of the herein invention appear to home to monocytes. It appears that monocytes and macrophages are an appropriate target for an antiviral agent directed to HIV or other retroviral infection. In AIDS patients, evidence of HIV-I infection has been observed in monocytes from a variety of tissues, including brain, peripheral blood, lymph nodes, skin, and lung (Pauza, C. D., et al, *J Virol* (1988) 62: (in press); Pauza, C. D., *Cell Immunol* (1988) 112:414-424) and human peripheral blood monocytes and monocyte-derived cell lines support viral replication in vitro. In addition, two other immunosuppressive retroviruses, MLDV and the Visna virus of ungulates, cause immunosuppression primarily by infecting monocytes.

Others have shown that monocytes act as a reservoir for virus in infection (Ho, D., et al, *New Eng J Med* (1987) 317:278-286; Klatzmann, D., et al, *Immunol Today* (1986) 7:291-296). Since few T-cells are actually infected with HIV-I in AIDS patients, and since it is known that infected monocytes can shed HIV-I envelope protein in soluble form, it is inferred that infected monocytes may mediate the loss of helper T-cells in these patients (Siliciano, R. F., et al, *Cell* (1988) 54:561-575).

The compounds of the present invention offer the capability to interfere with the life cycle of retroviruses in general, probably through interference with the activity of reverse transcriptase, and are thus useful as prophylactic and therapeutic agents in the treatment of retroviral infections.

DISCLOSURE OF THE INVENTION

The invention provides relatively nontoxic conjugates capable of inhibiting retroviral infection in human and animal subjects. The conjugates are toxic to the retrovirus, and appear to inhibit reverse-transcriptase.

Thus, in one aspect, the invention is directed to a method to treat or prevent retroviral infection in humans or other animals, which method comprises administering to a subject in need of such treatment an amount of a conjugate shown below which is effective in interrupting or preventing the virus infection.

Figure 2:
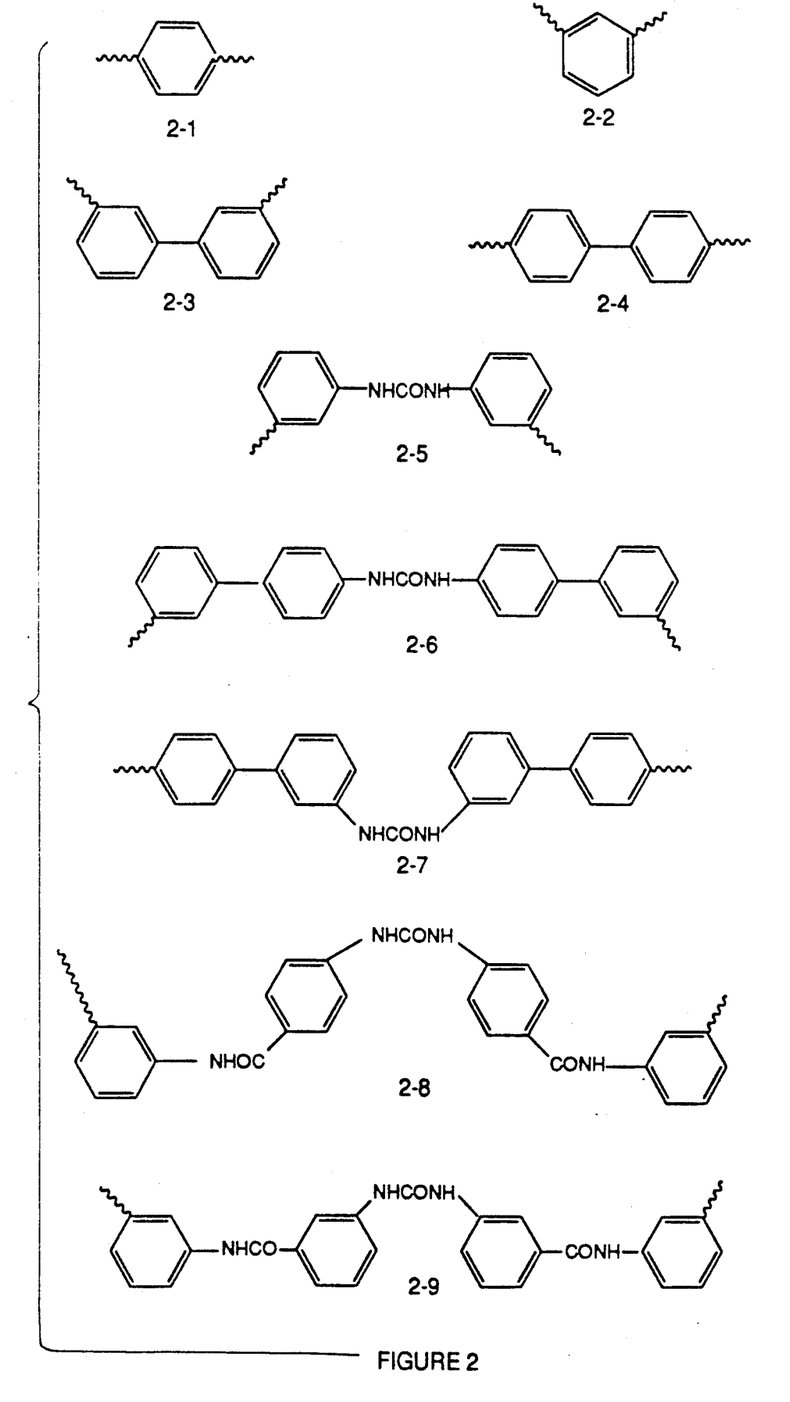
FIG. 2 shows typical embodiments of the moiety $R^2$ in the conjugates of the invention.

In another aspect, the invention is directed to the conjugates and the pharmaceutical compositions containing them. These conjugates are derivatives of the commercially available nontoxic dye, Lucifer Yellow CH, (LY-CH) and its analogs. In general, the conjugates are of the formula:

$$R-NHCONHN=C\diagup^{R^1}_{R^2} \quad (1)$$

wherein R is of the formula:

[structure with O=N=O naphthalene core, CO_3S and SO_3C substituents, and Z substituent]

wherein Z represents one or two non-interfering substituents, and C represents $H^+$ or a cation (or proportionate part thereof), and $R^1$ is H or alkyl (1-6C); and $R^2$ is alkyl (1-6C) or aryl (6-10C) or "linked" aryl (6-10C) containing 2-5 such aryl groups, said alkyl or aryl substituents being unsubstituted or substituted by 1-2 non-interfering groups. Some typical embodiments for $R^2$ are shown in FIG. 2.

In still another aspect, the invention is directed to a method to prepare the compounds of Formula 1 which comprises contacting a compound of the formula $RNHCONHNH_2$ with a compound of the formula $R^1R^2CO$, and recovering the resulting conjugate.

MODES OF CARRYING OUT THE INVENTION

A. Nature of the Precursors and Conjugates

The conjugates are derived from the nontoxic commercially available dye Lucifer Yellow (LY-CH) or its analogs. LY-CH has the formula:

[structure of LY-CH with NHCONHNH_2, naphthalimide core, $^-O_3S$, $SO_3^-$, and $NH_2$ substituents] LY-CH and is thus a semicarbazide. The commercially available material is in the form of the lithium salt; however, other salts of the sulfonates, or even the free acid forms, can be used in the formulation. Of course, the ionization status of the sulfonate will depend on the pH of the medium which surrounds it. Suitable salts for use when the compound is administered therapeutically include any nontoxic, inorganic ions, such as sodium, potassium, ammonium, calcium, magnesium, and so forth, or may also be organic cations, such as quaternary amines, e.g., diethylamine, triethylamine or ethanolamine. In general, inorganic ions are preferred, as these confer greater solubility on the compounds and are less expensive. The free acid form can also be used in the manufacture of a suitable formulation which will adjust the pH to a physiologically compatible value.

By "analogs" of the Lucifer Yellow moiety is meant compounds of the formula:

Ly-analog wherein Z represents one or two innocuous substituents in either ring such as lower alkyl, lower alkoxy, hydroxy, amino, thio, alkylamino, alkylthio, or halo. The nature of Z is not important in these analogs so long as it does not interfere with the self-assembly, with the efficacy of the conjugate, or with the non-toxicity of the precursor. Thus, by "analogs" of Lucifer Yellow, is meant those naphthalene disulfonates related to Lucifer Yellow which have different substituents in the naphthalene nucleus other than the single amino group present in Lucifer Yellow itself. As is the case with Lucifer Yellow, the analog sulfonates may be in the form the free acid or of any pharmaceutically acceptable salt.

Verification of the various parameters affecting dosage and administration can be obtained using a model system in cats involving feline immunosuppressive virus (FIV) which is a T-lymphotropic lentivirus, wherein the virus can infect feline T-lymphocytes, feline peripheral monocytes derived macrophages and CCL94 feline kidney-derived fibroblasts in vitro. As the symptoms of FIV are similar to those of AIDS infections in humans, this provides a suitable model system for this particular indication, as well as for retroviral infection in general (Pederson, N. C., et al, *Science* (1987) 235:790–793; Elder, J., (1988, personal communication)).

The cytotoxicity of Lucifer Yellow and the analogs within the scope of the invention is low. The $LD_{50}$ for LY-CH injected intravenously in mice is greater than 1 g/kg (Silverstein, S., (1987, personal communication)) and LY-CH exhibits no observable cytostatic activity in vitro against murine thiol-macrophages at 600 uM concentrations (Swanson, J. A., et al, *J Cell Biol* (1985) 100:851–859).

Preferred forms of the conjugates include those wherein R represents the tricyclic residue of Lucifer Yellow-i.e., Z is $NH_2$ at the position shown.

Preferred embodiments of $R^1$ are H and lower alkyl (1–4), most preferably H. By alkyl is meant a saturated hydrocarbyl of the indicated number of carbon atoms which is in a straight or branch chain form, such as methyl, ethyl, n-propyl, i-propyl, t-butyl, n-butyl, i-hexyl, n-hexyl, and 3-methylpentyl.

With respect to $R^2$, although $R^2$ can be alkyl, especially if $R^1$ is not H, conjugates in which $R^2$ is aryl are preferred. By aryl is meant a 6–10 membered monocyclic or fused bicyclic ring system which has aromatic character. The ring may contain only carbons as ring members, or which may contain one or more heteroatoms such as N. The aryl substituents are, thus, typically, moieties such as phenyl, pyridyl, naphthyl, quinolyl, pyrimidyl, and the like. The aryl substituents may contain 1–2 nonhydrogen substitutions which do not interfere with the pharmacological effect of the conjugate. Typical substituents include, but are not limited to, lower alkyl, lower alkoxy, hydroxy, amino, thio, alkyl amino, alkyl thio, halo, carboxy, carbalkoxy, or CHO.

The substituent $R^2$ may also include multiple "linked" aryl (or, perhaps, more properly, arylene substituents wherein a total of 1–5 aryl moieties of 6–10C are linked through nonaromatic substituents or through a covalent bond to form an extended chain of aryl groups. Perhaps the simplest example of this is the embodiment of $R^2$ is biphenyl wherein two phenyl groups are linked through a single covalent bond. Other examples of this type of "necklace" of aryl moieties is found in FIG. 2, wherein in some instances phenyl groups are linked through —CONH— or —NHCONH—. Other types of linkage include hydrocarbylene linkages and conjugation-type linkages through —CH=CH—. As is the case for a single aryl substituent, the aryl groups forming the extended chain may be substituted with 1–2 non-interfering substituents. A particularly preferred is —CHO. Particularly preferred also are those embodiments wherein at least two linked aryl groups are present in the substituent $R^2$, and most preferred is the substituent which is a substituted biphenyl shown as Formula 2-4 in FIG. 2.

Thus, particularly preferred as conjugates are those derived from Lucifer Yellow CH itself, in the form of any pharmaceutically acceptable salt, as the compound of formula 3, and the compound of the formula:

i.e., those of the formula (A4)

Figure 3:
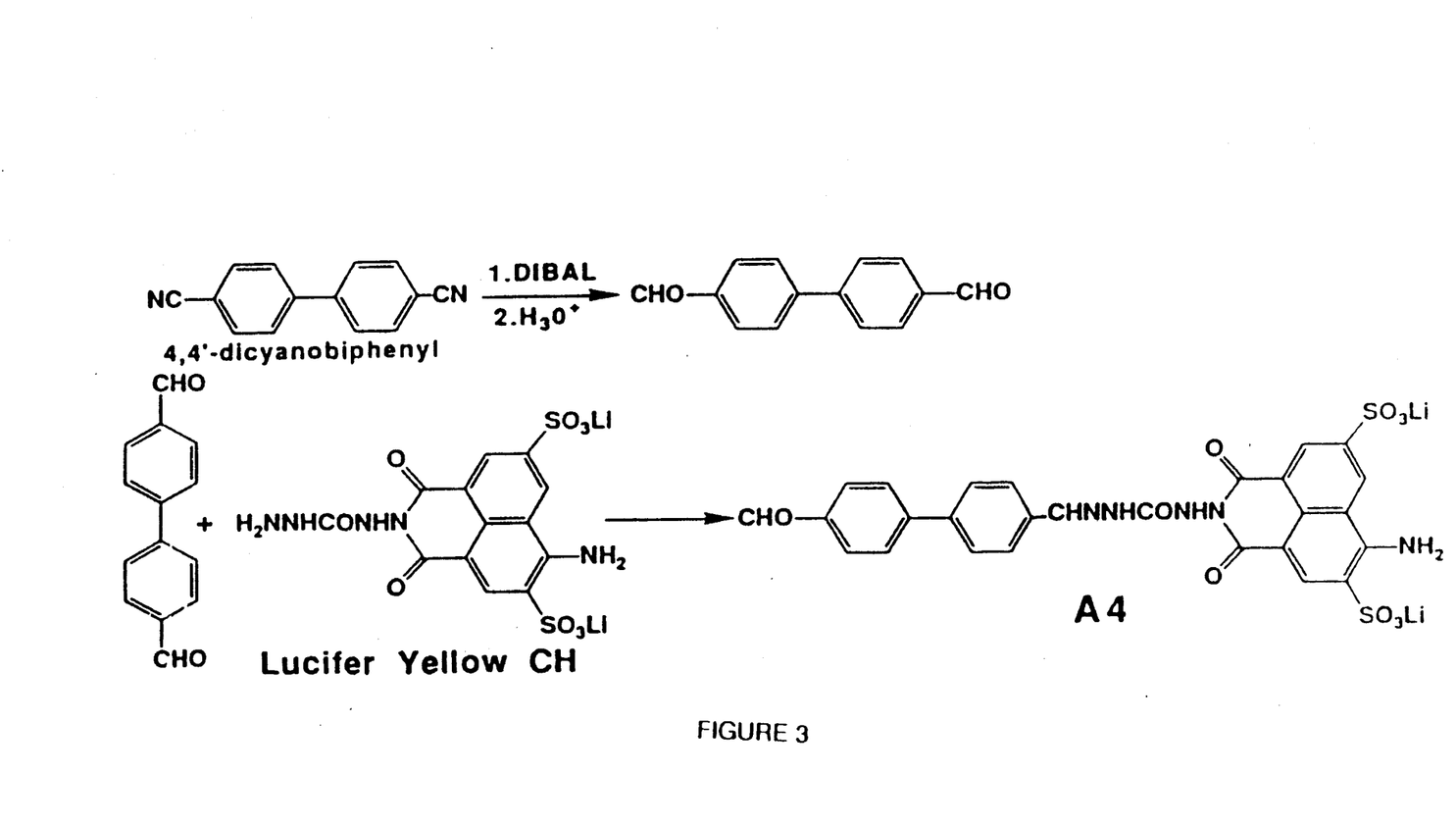
FIG. 3 shows the synthesis of the conjugate A4.
Figure 4:
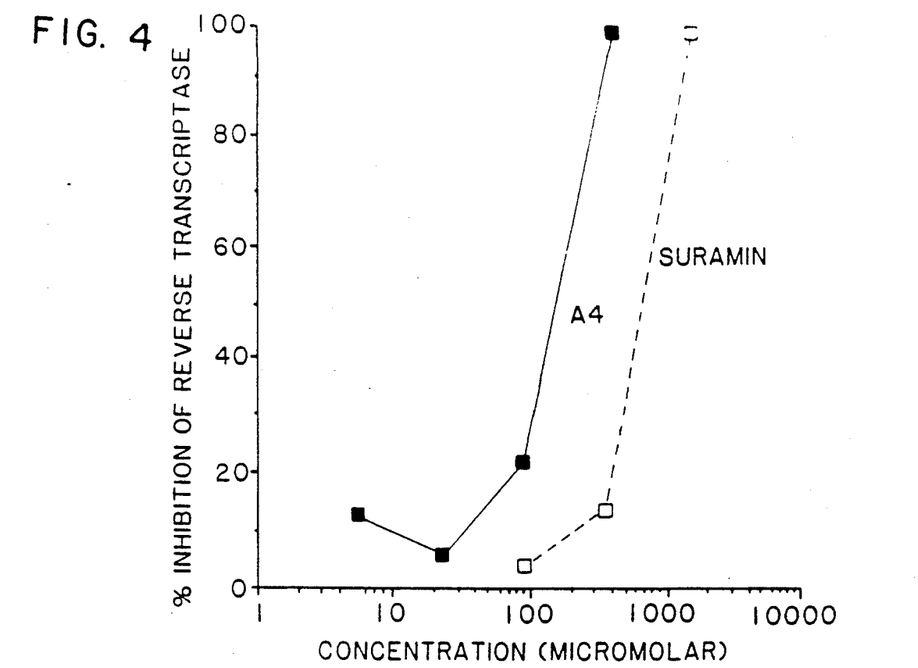
FIG. 4 shows the effect of A4 and suramin on inhibition of reverse-transcriptase isolated from HIV-1.
Figure 5:
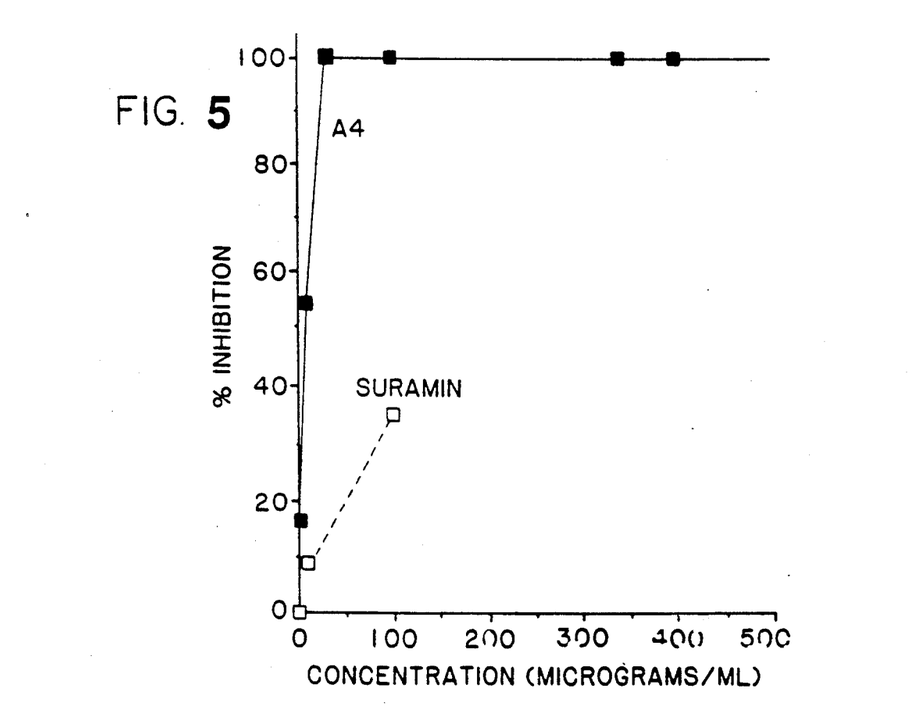
FIG. 5 shows the effect of suramin and A4 to inhibit reverse transcriptase isolated from feline immunodeficiency virus (FIV).
Figure 6:
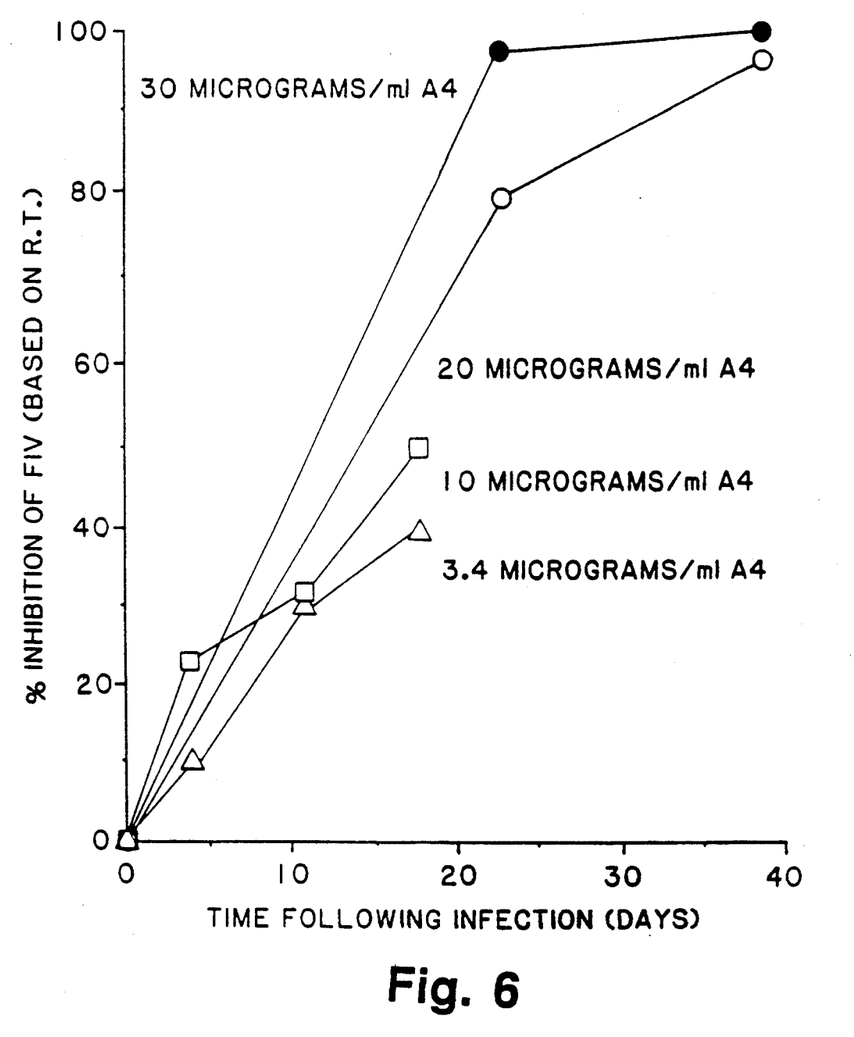
FIG. 6 shows the inhibition of growth of FIV in feline kidney cells by the invention compound A4.
Figure 7:
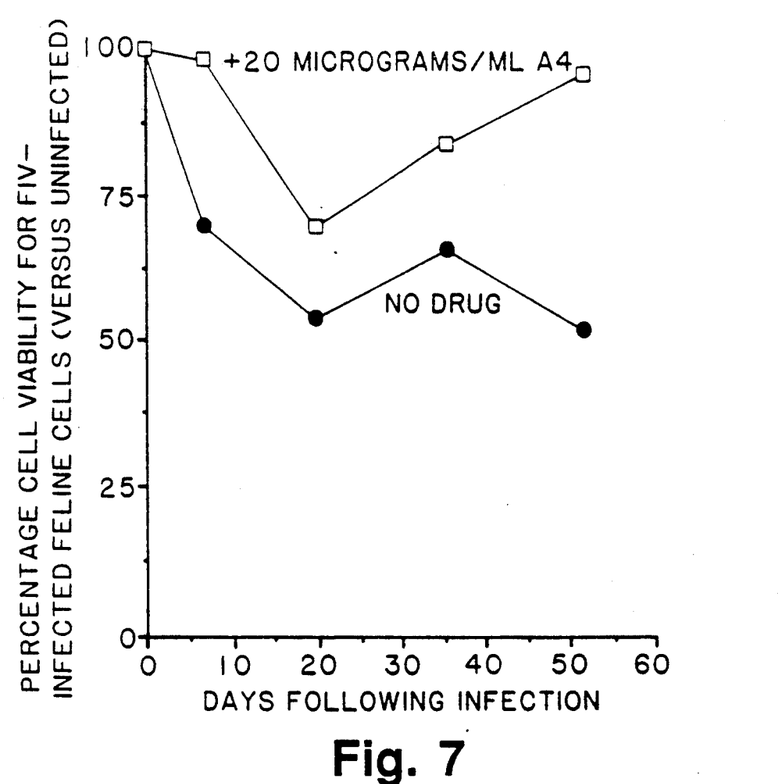
FIG. 7 shows the effect of A4 on the viability of infected feline cells containing FIV.
Figure 8:
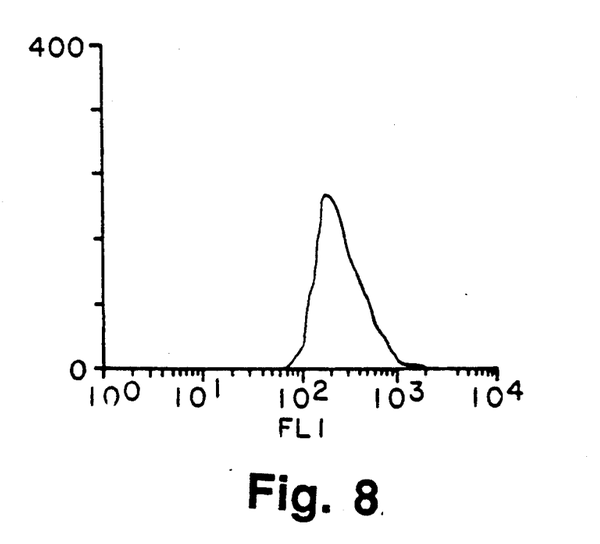
FIG. 8 shows the results of fluorescence activated-cell sorting (FACS) demonstrating that A4 is taken up and retained by a human macrophage-like cell line U937.

The synthesis of A4 from commercially available reagents is outlined in FIG. 3. As shown in FIG. 3, the commercially available compound 4,4'-dicyanobiphenyl is reduced in DIBAL and hydrolyzed to obtain the dialdehyde. The dialdehyde is then reacted with the lithium salt of Lucifer Yellow in a controlled reaction to obtain the single conjugate A4, which is then isolated using standard chromatographic methods. The lithium salt, is, if desired, converted to alternate pharmaceutically acceptable nontoxic salts.

B. Selectivity for Monocytes and Derivati

Lucifer Yellow itself is a nontoxic, fluorescent, membrane-impermeable dye (Stewart, W. W., *Cell* (1978) 14:741) which is taken up by monocyte/macrophage endosomes through pinocytosis and is concentrated in the lysosomes. The rate of pinocytosis and accumulation in lysosomes is higher for macrophages, especially activated macrophages, than for other cell types such as fibroblasts (Besterman, J. M., et al, *J Cell Biol* (1981) 91:916-917; Steinman, R. M., et al, *J Cell Biol* (1976) 68:665-687) and does not bind to proteins to a substantial degree. The analogs of Lucifer Yellow which are within the scope of this invention exhibit similar properties. Because no specific receptor interaction is involved in the uptake of Lucifer Yellow by monocytes, these analogs which retain the membrane impermeable nature of LY-CH are similarly taken up by the lysosomes. In addition, unlike suramin, the LY-CH and analog-derived conjugates of the invention are not bound to serum proteins Thus, their bioavailability is not diminished in this way.

Thus, the conjugates derived from Lucifer Yellow and its analogs are expected to home to the virus-tropic cells, such as monocytes, rather than to the non-tropic cells, for example neutrophils. In addition, as the Lucifer Yellow-derived conjugates are concentrated in the lysosomes. Concentration of the precursors in the desired target cells results, of course, in magnified selectivity.

C. Formulation and Administration

As the conjugates are to be administered as pharmaceuticals, they are formulated in a conventional manner and administered either localized at the targeted site or systemically. Generally known methods of formulation are employed, including sustained-release matrices, conventional excipients, and simple solutions, as described, for example, in *Remington's Pharmaceutical Sciences* (latest edition), Mack Publishing Company, Easton, Pa. Systemic administration is feasible in using the conjugates as treatment for retroviral infection, since it is known that LY-CH is taken up and concentrated in the endosomes and lysosomes of macrophages. This has been reported for murine thiol-elicited macrophages This results in a concentration of the conjugate in T-cells which contact macrophages, as opposed to kidney or other parts of the body. The compound thus tends to accumulate and react in locations where the virus infection is likely to be found.

The conjugates can be administered intravenously, intramuscularly, orally, or intraperitoneally, at about 1-1000 mg/kg body weight.

The dosage level required depends, of course, on the choice of specific conjugate, as well as the nature of the subject being treated for retroviral infection and the magnitude of the infection or the potential therefor. Administration may have either therapeutic or prophylactic effects or both. For most embodiments, a dosage of the conjugate on the order of 0.1-5 g/week appears suitable.

In a preferred approach, by derivatizing the conjugates so as to administer them in particulate form, for example, by conjugating them to a carbohydrate, selective killing of the macrophage cells which harbor the virus can be accomplished. Because the drugs are perceived as particles, they will be readily attacked by the macrophages.

The following examples are intended to illustrate, but not to limit, the invention.

EXAMPLE 1

Effect of A4 on HIV and FIV

Compound A4 was first tested for its ability to inhibit reverse transcriptase isolated either from HIV-1 or from FIV using a standard protocol. The results are shown in FIGS. 4 and 5 for HIV-1 and FIV respectively. In each case, A4 was more potent than suramin in inhibiting the enzyme. The approximate $IC_{50}$ values are 200 uM against HIV-1 and 20 uM against FIV.

A4 was also tested for its ability to inhibit the growth of FIV in a culture containing feline kidney cells using standard assays. As shown in FIG. 6, using a concentration of 30 ug/ml A4, FIV growth and proliferation were virtually completely inhibited within 20 days following infection; administration of 20 ug/ml A4 resulted in corresponding inhibition 40 days thereafter. Smaller concentrations had similar effects but were less dramatic The results in FIG. 7 show the effect of A4 (20 ug/ml) on the viability of infected cells. This concentration of A4 was able to reestablish 100% viability of the infected cells within 50 days of infection.

Finally, FIG. 8 shows that the macrophage cell line U937 takes up and retains A4.

In an in vivo test, compound A4 was injected into two mice interperitoneally at a dose of 60 mg/kg. No apparent toxicity was evident 15 days later, showing that the conjugate is relatively non-toxic.

We claim:

1. A method to inhibit viral proliferation in cells infected with retrovirus which method comprises contacting said cells with a conjugate of the formula:

wherein R has the formula:

in which Z represents one or two non-interfering substituents;

and wherein $R^1$ is H or alkyl (1-6C); and aryl (6-10C) containing 2-5 such aryl groups, said alkyl or aryl substituents being unsubstituted or substituted by 1-2 non-interfering groups;

or the pharmaceutically acceptable salts thereof.

2. The method of claim 1 wherein the conjugate is of the formula:

(2)

wherein R is as defined in claim 1.

3. The method of claim 2 wherein the conjugate is of the formula or the pharmaceutically acceptable salts thereof.

4. The method of claim 1 wherein said retrovirus is feline immunodeficiency virus (FIV).

5. A compound of the formula:

wherein R has the formula:

in which Z represents one or two non-interfering substituents, and wherein $R^1$ is H or alkyl (1–6C) and

$R^2$ is alkyl (1–6C) or aryl (6–10C) containing 2–5 such aryl groups, said alkyl or aryl substituents being unsubstituted or substituted by 1–2 non-interfering groups; and the pharmaceutically acceptable salts thereof.

6. A compound of claim 5 which has the formula wherein R is as defined as in claim 4.

7. The compound of claim 6 which is of the formula

* * * * *

UNITED STATES PATENT AND TRADEMARK OFFICE
CERTIFICATE OF CORRECTION

PATENT NO. : 5,177,083
DATED : January 5, 1993
INVENTOR(S) : Darryl C. Rideout et al.

It is certified that error appears in the above-indentified patent and that said Letters Patent is hereby corrected as shown below:

In column 8, line 65, following "(1-6C); and", insert
--$R^2$ is alkyl (1-6C) or aryl (6-10C) or linked--.

Signed and Sealed this

Twenty-second Day of August, 1995

Attest:

BRUCE LEHMAN

Attesting Officer

Commissioner of Patents and Trademarks